(12) United States Patent
Hahn et al.

(10) Patent No.: US 11,992,314 B2
(45) Date of Patent: May 28, 2024

(54) CONTINUOUS GLUCOSE MONITORING SYSTEM

(71) Applicants: FIRSTTECH INCORPORATION, Daegu (KR); INDUSTRIAL COOPERATION FOUNDATION JEONBUK NATIONAL UNIVERSITY, Jeonju Jeollabukdo (KR)

(72) Inventors: YoonBong Hahn, Jeonju Jeollabukdo (KR); Yongkyu Park, Jeonju Jeollabukdo (KR); Yongwoo Oh, Incheon (KR); Sanghyeok Seo, Daegu (KR); Hoseong Kwak, Daegu (KR)

(73) Assignees: FIRSTTECH INCORPORATION, Daegu (KR); INDUSTRIAL COOPERATION FOUNDATION JEONBUK NATIONAL UNIVERSITY, Jeonju Jeollabukdo (KR)

( * ) Notice: Subject to any disclaimer, the term of this patent is extended or adjusted under 35 U.S.C. 154(b) by 0 days.

(21) Appl. No.: 18/073,749

(22) Filed: Dec. 2, 2022

(65) Prior Publication Data
US 2023/0293066 A1   Sep. 21, 2023

(30) Foreign Application Priority Data
Dec. 22, 2021 (KR) .................. 10-2021-0184920

(51) Int. Cl.
A61B 5/1473 (2006.01)
A61B 5/00 (2006.01)
A61B 5/145 (2006.01)

(52) U.S. Cl.
CPC ........ *A61B 5/1473* (2013.01); *A61B 5/14532* (2013.01); *A61B 5/685* (2013.01)

(58) Field of Classification Search
CPC .... A61B 5/1473; A61B 5/14532; A61B 5/685
See application file for complete search history.

(56) References Cited

U.S. PATENT DOCUMENTS

2006/0264716 A1* 11/2006 Zander ............... A61B 5/14865
29/854
2013/0337567 A1* 12/2013 Shin ....................... H01L 29/78
436/63

(Continued)

FOREIGN PATENT DOCUMENTS

KR  1020190038660 A   4/2019
KR  1020190073084 A   6/2019

(Continued)

*Primary Examiner* — Jay B Shah
*Assistant Examiner* — Meghan R Kumar
(74) *Attorney, Agent, or Firm* — NKL LAW; Jae Youn Kim

(57) ABSTRACT

The present invention relates to a continuous glucose monitoring system that is capable of continuously monitoring blood glucose levels. According to the present invention, the continuous glucose monitoring system includes: a body (A) attached to a given region of a user's body having less pain; a glucose sensor (B) having a micro needle (B1) protruding from one surface of the body (A) to be inserted into the epidermis of the user's body; and a glucose monitoring module (C) for monitoring the glucose from the glucose sensor (B).

1 Claim, 4 Drawing Sheets

(56) References Cited

U.S. PATENT DOCUMENTS

| | | | | |
|---|---|---|---|---|
| 2016/0058474 A1* | 3/2016 | Peterson | ............ | A61B 5/14503 |
| | | | | 600/347 |
| 2016/0278672 A1* | 9/2016 | Cho | ................ | A61B 5/1473 |
| 2021/0030360 A1* | 2/2021 | Huang | ................ | A61B 5/1451 |
| 2021/0379282 A1* | 12/2021 | O'Connor | ......... | A61M 5/14248 |

FOREIGN PATENT DOCUMENTS

| KR | 1020200011369 A | 2/2020 |
|---|---|---|
| KR | 1020210021726 A | 3/2021 |
| KR | 1020210046904 A | 4/2021 |
| KR | 1020210062285 A | 5/2021 |
| KR | 1020210064651 A | 6/2021 |

* cited by examiner

CONTINUOUS GLUCOSE MONITORING SYSTEM

CROSS REFERENCE TO RELATED APPLICATION OF THE INVENTION

The present application claims the benefit of Korean Patent Application No. 10-2021-0184920 filed in the Korean Intellectual Property Office on Dec. 12, 2022, the entire contents of which are incorporated herein by reference.

BACKGROUND OF THE INVENTION

Field of the Invention

The present invention relates to a continuous glucose monitoring system that is capable of continuously monitoring blood glucose levels.

Background of the Related Art

Diabetes is a metabolic disease that is characterized by a high blood glucose level over a prolonged period of time, and about 500 million people worldwide have diabetes. If the pancreas does not produce enough insulin owing to various factors such as obesity, stress, wrong eating habits, heredity, and the like to thus fail to hold the balance of glucose in blood, an amount of glucose in blood absolutely increases to cause the occurrence of diabetes.

A given concentration of glucose is contained in blood, and the cells of the body obtain energy from the glucose. If an amount of glucose excessively increases, the glucose is not properly stored in the liver, muscles, or fat cells, and the like, but accumulated in blood. As a result, a diabetic patient has a significantly higher glucose level than a normal person, and the excessive amount of glucose just passes through tissues of the body and is discharged together with urine, so that glucose absolutely needed for the tissues of the body is insufficient to cause the tissues of the body to become abnormal.

Early stage diabetes has rare subjective symptoms, but if the disease is developed, it causes specific signs such as increased thirst, unexplained hunger, frequent urination, loss of weight, tiredness, itching, slow healing of cuts and wounds in the hands or feet. Further, if diabetes is seriously developed, it causes complications such as visual disturbance, hypertension, nephropathy, stroke, periodontal disease, muscle spasm, neuralgia, gangrene, and the like.

To diagnose diabetes and to prevent the diabetes from developing the complications, a system for monitoring blood glucose levels is needed together with a treatment for diabetes.

According to a conventional glucose monitoring device, generally, a user extracts blood from a patient's fingertip to monitor his or her blood glucose level per one time.

However, the diabetic patient may have high blood glucose levels and low blood glucose levels several times a day, and if he or she is unexpectedly kept at the low blood glucose levels over a long period of time, he or she may lose his or her consciousness or life. Accordingly, the method for intermittently monitoring the blood glucose levels may cause the risk of the patient because his or her low blood glucose levels are not immediately monitored.

Further, the blood extraction type glucose monitoring device is configured to insert a needle into a fingertip sensitive to pain so as to extract a diabetic patient's blood and monitor his or her own glucose level, thereby undesirably causing a serious pain and making him or her feel reluctant to perform the blood extraction.

Moreover, the monitoring principle of the blood extraction type glucose monitoring device makes use of a reduction-oxidation reaction between glucose oxidase enzyme and glucose, but as time passes, the characteristics of the glucose oxidase enzyme may become deteriorated, thereby failing to continuously monitor the blood glucose levels.

For the reference, the following four prior art literatures are found in patent information net, Korea Intellectual Property Rights Information Service (KPRIS), with keyword "blood glucose monitoring", and the technical field and background of the present invention will be appreciated when referring to the following prior art literatures.

Prior art literatures: Korean Patent Application Laid-open Nos. 1020210064651, 1020210062285, 1020210046904, and 1020210021726

SUMMARY OF THE INVENTION

Accordingly, the present invention has been made in view of the above-mentioned problems occurring in the related art, and it is an object of the present invention to provide a continuous glucose monitoring system that is capable of continuously monitoring blood glucose levels, especially without any blood extraction.

It is another object of the present invention to provide a continuous glucose monitoring system that is capable of continuously monitoring blood glucose levels, without any blood extraction, while adopting a transistor-based non-enzymatic micro needle glucose sensor (as disclosed in Korean Patent Application Laid Open No. 10-2021-0023041) as filed by the same applicant as the invention.

To accomplish the above-mentioned objects, according to the present invention, there is provided a continuous glucose monitoring system including: a body attached to a given region of a user's body having less pain; a glucose sensor having a micro needle protruding from one surface of the body to be inserted into the epidermis of the user's body; and a glucose monitoring module for monitoring the glucose from the glucose sensor.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Figure 1:
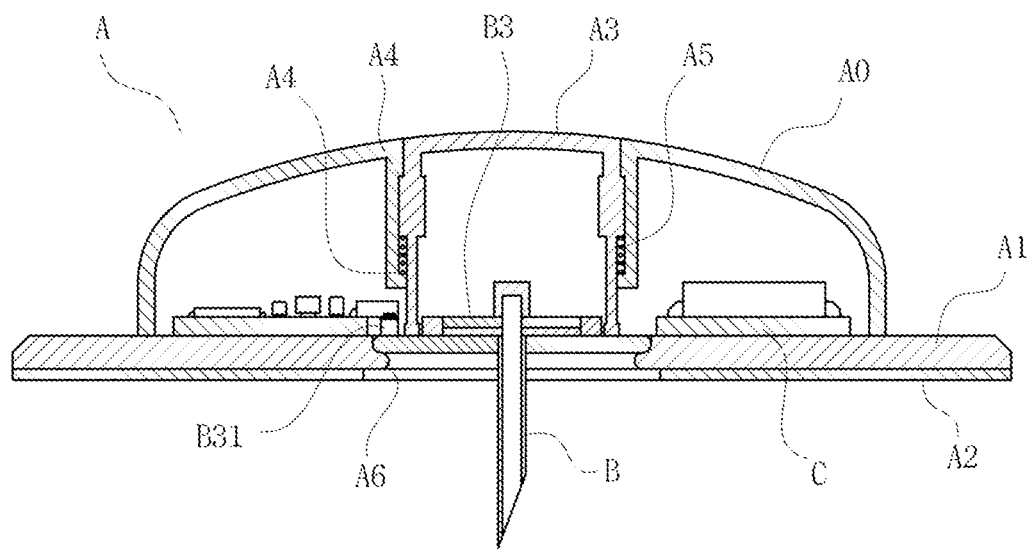
FIG. 1 is a sectional view showing a continuous glucose monitoring system according to the present invention.

Hereinafter, embodiments of the present invention will be explained in detail with reference to the attached drawings. In the drawing figures, main components may be exaggerated, omitted, or schematically shown for the conveniences of explanation, and terms as will be discussed in the description are defined in accordance with the shapes and functions of the present invention, not as dictionary meaning. Directions are determined with respect to the direction initially suggested in the drawings, and positions are determined with respect to the intermediate portion of respective components or the center of a circle. Detailed explanations of prior art technologies and conventional technologies may be omitted or replaced with simple reference numerals or names for the clarity of the description. Further, the detailed structure, shape, arrangement, size and the like of the part identified in the drawings and the operation and effect of the part inferred in the drawings may be omitted for the clarity of the description. Moreover, bolts, welded portions, holes, and the like that are applied to couple parts to each other may be omitted in the drawings for the clarity of the description. The part unless defined herein may have a circular or square shape on plane, and in this case, the plan view of the part may be omitted.

Now, an embodiment of the present invention will be explained with reference to FIGS. 1 to 3.

As shown in FIG. 1, a continuous glucose monitoring system according to the present invention includes: a body A attached to a given region of a user's body having less pain; a glucose sensor B having a micro needle B1 protruding from one surface of the body A to be inserted into the epidermis of the user's body; and a glucose monitoring module C for monitoring the glucose from the glucose sensor B.

In specific, as shown in FIG. 1, the body A includes: a series of casings A0 having the shape of a circular plate; an attachment plate A1 disposed on one surface of the casings A0 and attached to the given region of the user's body; and an adhesion pad A2 disposed on the underside of the attachment plate A1, and the glucose sensor B is disposed inside the casings A0 to allow the micro needle B1 to protrude outward from the center of the attachment plate A1. Further, the glucose monitoring module C for monitoring the glucose from the glucose sensor B is disposed inside the casings A0.

Figure 2:
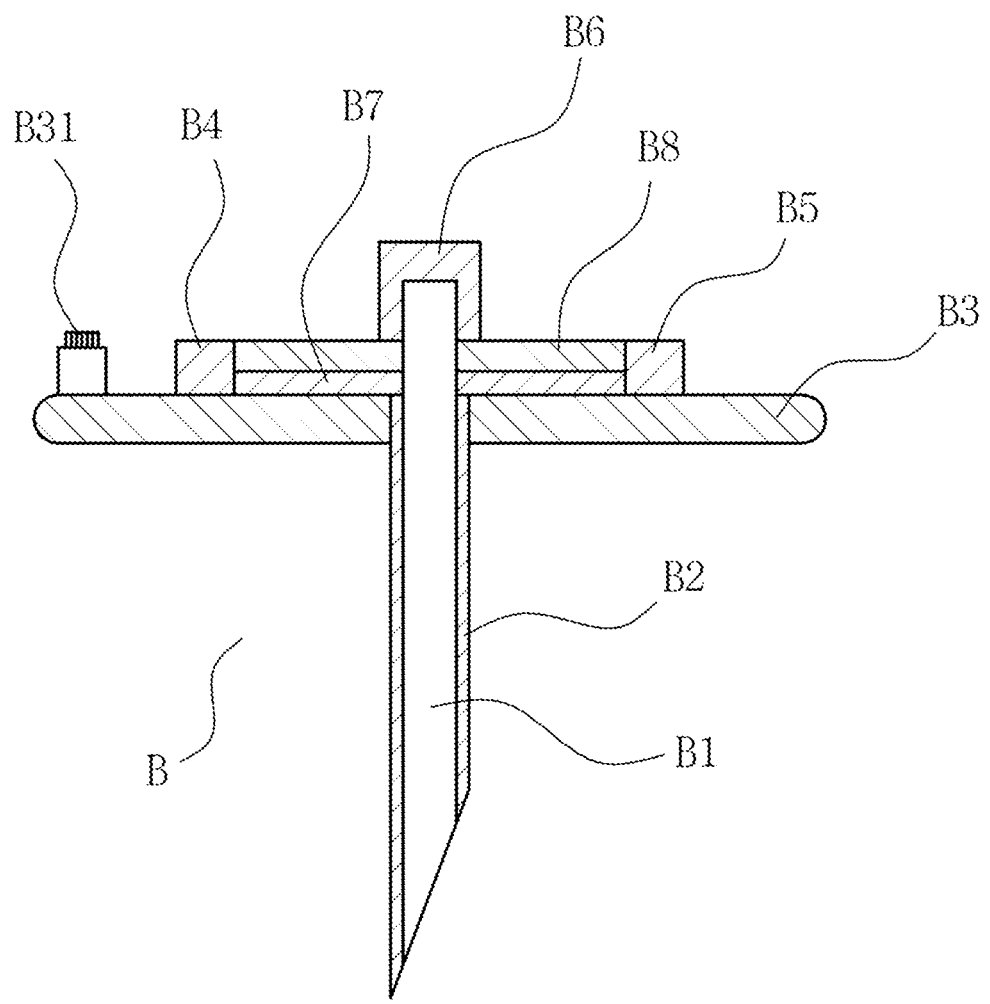
FIG. 2 is an enlarged view showing the glucose sensor of FIG. 1.

Further, as shown in FIG. 2, the glucose sensor B includes: the micro needle B1 disposed at the end thereof and coated with an oxide layer B2; one side source electrode B4 and the other side drain electrode B5 connected to top of a substrate B3 to have conductivity to one end of the micro needle B1 where the oxide layer B2 is not coated; and a gate electrode B6 connected to one end of the micro needle B1 where the oxide layer B2 is not coated on the substrate B3 and insulated from one side source electrode B4 and the other side drain electrode B5.

Figure 3:
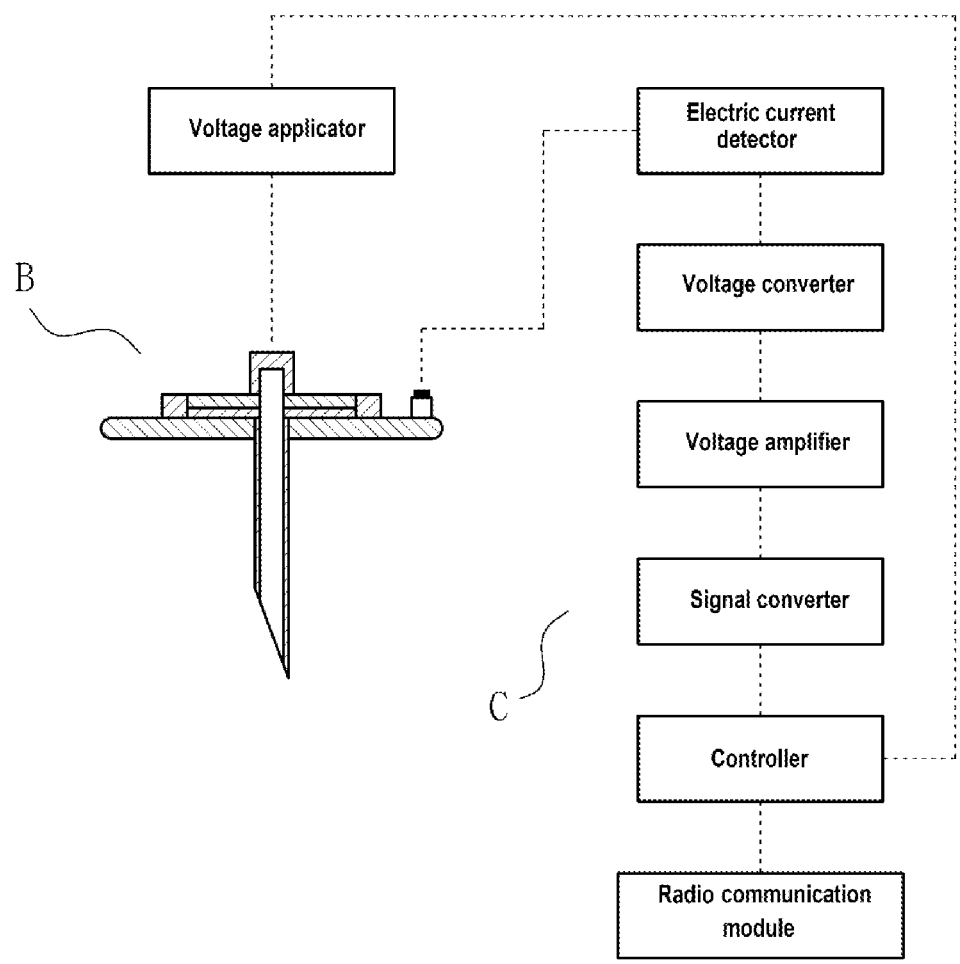
FIG. 3 is a block diagram showing the glucose monitoring module of FIG. 1.

Further, as shown in FIG. 3, the glucose monitoring module C includes: a voltage applicator connected between the gate electrode B6 of the glucose sensor B and the glucose monitoring module C; an electric current detector connected to a space between the source electrode B4 and the drain electrode B5 to detect an electric current; a voltage converter for converting the electrical current of the electric current detector into a voltage; a voltage amplifier for amplifying the voltage of the voltage converter; a signal converter for converting an analog signal of the voltage of the voltage amplifier into a data signal; a controller for identifying the data signal of the signal converter; and a radio communication module for transmitting the signal of the controller to the outside.

In specific, as shown in FIG. 1, the body A includes: a button A3 pressurized downward from the center of the casings A0; a stepped protrusion A4 for restricting an up and down moving distance of the button A3 from the casings A0; an elastic member A5 adapted to elastically support the button A3 against the stepped protrusion A4; a locking projection A6 protruding from the attachment plate A1 to lock the underside of the substrate B3 of the glucose sensor B onto the attachment plate A1; and a connection terminal B31 connected to the glucose monitoring module C when the glucose sensor B is located on top of the locking projection A6 of the attachment plate A1.

To have a configuration of an electronic terminal, further, the body A may include a battery, a power supply, and a radio communication module disposed therein and a display panel, a control panel, a battery charging terminal, and a communication connection terminal disposed thereon, which are not shown in the drawings.

Further, an attachment tool for attaching the body A to the given region of the user's body, without any pain, and a fixing belt for firmly maintaining the attached state of the body A to the given region may be further provided, which are not shown in the drawings.

As shown, further, the glucose sensor B includes: the micro needle B1 having a conductive core whose one of the ends is keen and the oxide layer B2 coated on the entire outer peripheral surface of the core excepting end portions of the core; the substrate B3 allowing one of the end portions of the micro needle B1 to protrude upward therefrom and the other one of the end portions to protrude outward therefrom; a conductive member B7 coatedly connected from top of the substrate B3 to the oxide layer B2; the source electrode B4 disposed at one side of the conductive member B7; the drain electrode B5 disposed at the other side of the conductive member B7; an insulation layer B8 coated on top of the conducive member B7 to connect the source electrode B4 and the drain electrode B5; and the gate electrode B6 disposed at one end of the core of the micro needle B1 to allow the source electrode B4 and the drain electrode B5 to be spaced apart from top of the insulation layer B8.

For more detailed configuration of the glucose sensor B, a "transistor-based non-enzymatic micro needle glucose sensor and manufacturing method thereof" (as disclosed in Korean Patent Application Laid Open No. 10-2021-0023041) as filed by the same applicant as the invention is suggested for reference.

Moreover, the voltage applicator of the glucose monitoring module C may be a circuit with precision resistors connected in series, the electric current detector may be a circuit or IC chip with shunt precision resistors, the voltage converter may be a circuit or IC chip with combination precision resistors, the voltage amplifier may be a circuit or IC chip with precision resistors, the signal converter may be an A/D converter, the controller may be a processor, an IC chip, or the like, and the radio communication module may be Bluetooth.

Further, the glucose monitoring module C has the shape of a doughnut-shaped substrate so that it may be mounted in the body A.

Figure 4:
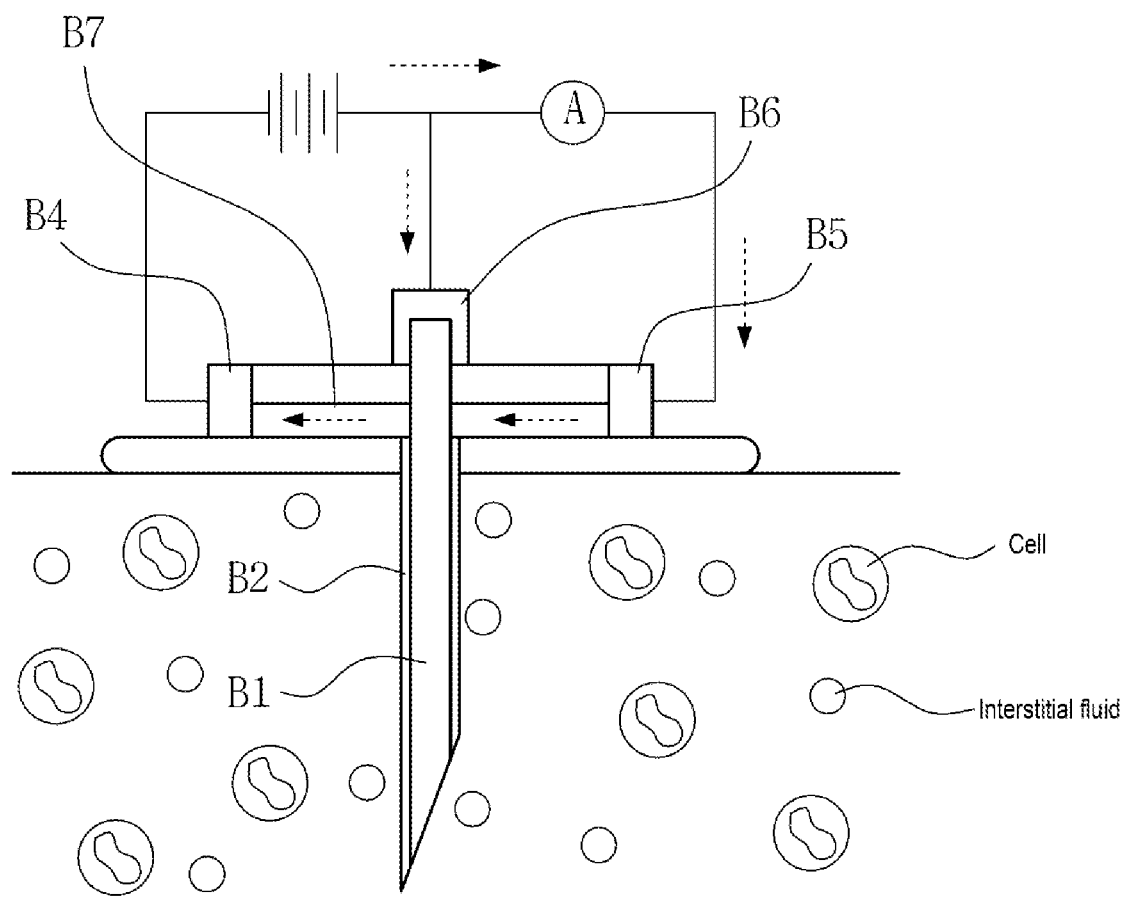
FIG. 4 is a schematic view showing a method for using the continuous glucose monitoring system of FIG. 1 and a glucose monitoring principle.

Hereinafter, a method for using the continuous glucose monitoring system according to the present invention and a glucose monitoring principle will be explained with reference to FIG. 4.

As shown, the body A is attached to the given region of the user's body, such as the underbelly, which makes him or her feel less pain and is not cumbersome in his or her movements, while the glucose sensor B is being inserted by about 2 mm into his or her skin.

If the micro needle B1 comes into contact with an interstitial fluid in the epidermis, a reduction-oxidation reaction occurs between the oxide layer B2 coated on the periphery of the micro needle B1 and interstitial fluid glucose, and in this case, the glucose is oxidized to form gluconolactone. As a by-product of the reaction, hydrogen peroxide ($H_2O_2$) is produced.

In this case, for example, if a voltage of 0.4 to 0.6 V is applied to the gate electrode B6, hydrogen peroxide ($H_2O_2$) is reduced to generate electrons, and the generated electrons move to the conductive members B7 along the micro needle B1 to generate an electric current between the source electrode B4 and the drain electrode B5.

The electric current generated is detected by the glucose monitoring module C, and the detected electric current is converted into a voltage. Next, the converted voltage is amplified, the amplified voltage is converted into data signal, and the converted signal is identified.

If glucose concentration in the interstitial fluid is high, an amount of hydrogen peroxide ($H_2O_2$) produced may become large upon the oxidization of the glucose, and accordingly, the number of electrons generated upon the dissolution of hydrogen peroxide ($H_2O_2$) becomes increased to cause a strong electric current to be generated between the source electrode B4 and the drain electrode B5. Contrarily, if glucose concentration in the interstitial fluid is low, an amount of hydrogen peroxide ($H_2O_2$) produced may become small upon the oxidization of the glucose, and accordingly, the number of electrons generated upon the dissolution of hydrogen peroxide ($H_2O_2$) becomes decreased to cause a weak electric current to be generated between the source electrode B4 and the drain electrode B5.

As a result, the intensity of electric current generated between the source electrode B4 and the drain electrode B5 becomes determined according to the glucose concentration in the interstitial fluid, so that it is possible that the glucose concentration is monitored from the intensity of electric current.

It is possible that glucose concentration is monitored through the reaction between the oxide layer B2 of the micro needle B1 of the glucose sensor B and the glucose, without having any glucose oxidase enzyme, and unlike the glucose oxidase enzyme, further, the characteristics of the oxide layer B2 are not deteriorated even if environments are varied or time passes, so that it is possible that glucose concentration is continuously monitored accurately.

The monitored glucose level is transmitted to the user's smartphone and insulin pump through the radio communication module such as Bluetooth, so that insulin is supplied to him or her according to his or her glucose level, and further, the insulin pump is controlled by his or her smartphone. Through the smartphone, further, his or her health state, his or her glucose level statistics, and his or her treatment period can be checked and managed.

As described above, the continuous glucose monitoring system according to the present invention is configured to allow the body A having the micro needle B1 to be attached to the given region of the user's body where he or she feels less pain so as to monitor the glucose from the interstitial fluid in the epidermis, thereby having no need to perform the blood extraction causing pain in the conventional practices, to allow the micro needle B1 to be inserted into the epidermis, thereby reducing the intensity of pain, and to allow the body A to be kept at the attached state to the user's body, thereby continuously monitoring the blood glucose levels and checking glucose changes in real time.

Further, it is easy to attach the body A to the given region of the user's body, and if the glucose sensor B is contaminated, the glucose sensor B is removed from the body A and exchanged into new one.

Moreover, the glucose sensor B is a field effect transistor-based non-enzymatic glucose sensor for sensing blood glucose levels by detecting the electric current, without having any glucose oxidase enzyme.

Additionally, the glucose monitoring module C serves to detect and amplify the electric current of the glucose sensor B and easily identify the glucose level, and through the radio communication module, glucose management history on the user's smartphone is seen and the insulin pump is controlled conveniently.

The foregoing description of the embodiment of the invention has been presented with reference to the drawings to help the principle of the configuration of the present invention understood, and the configuration of the present invention and the components in the configuration are determined in structure, shape, arrangement, direction, and numbers, and if necessary, they will be freely changed. The configuration and components of the present invention may be most desirably suggested to obtain the effectiveness of the present invention from a person having ordinary skill in the art. Accordingly, it is most desirable that the components are all included in the present invention, but some of them may be selected or removed according to cost reduction, conveniences in manufacturing process, environmental conditions, and necessities. Otherwise, one or some of the components is (are) separated and combined with other components. The above-mentioned components may be applied independently of one another in a different technical field from the technical field herein in consideration of the principle, purpose, function, role, operation, and effectiveness. Accordingly, the scope of the invention is defined in order of claims having relatively wide right, and from the description and the claims appended hereto, a subject of the invention may be sufficiently recognized by a person having ordinary skill in the art. Also, the operating effects generated from some components not explained, even if they have been illustrated will be sufficiently inferred from the drawings. Persons skilled in the relevant art can appreciate that many modifications and variations are possible in light of the above teachings, and accordingly, the development of the technical field and the use efficiency will be more improved.

What is claimed is:

1. A continuous glucose monitoring system comprising:
   a body configured to be attached to a given region of a user;
   a glucose sensor having a micro needle protruding from one surface of the body and configured to be inserted into an epidermis of the user; and
   a glucose monitoring module for monitoring glucose from the glucose sensor, wherein the body comprises: a series of casings having a shape of a circular plate;
   an attachment plate disposed on one surface of the series of casings and configured to be attached to the given region of the user;
   an adhesion pad disposed on an underside of the attachment plate,
   wherein the glucose sensor is disposed inside the series of casings to allow the micro needle to protrude outward from a center of the attachment plate, wherein the glucose monitoring module is disposed inside the series of casings;
   a button to be pressurized downward from a center of the series of casings;
   a stepped protrusion for restricting an up and down moving distance of the button from the series of casings;

an elastic member adapted to elastically support the button against the stepped protrusion;

a locking projection protruding from the attachment plate to lock the underside of a substrate of the glucose sensor onto the attachment plate; and a connection terminal connected to the glucose monitoring module when the glucose sensor is located on top of the locking projection of the attachment plate, wherein the glucose sensor comprises: the micro needle including a conductive core having an outer peripheral surface, a lower end of the conductive core, a upper end of the conductive core, and an oxide layer coated on the entire outer peripheral surface of the conductive core except end portions of the conductive core including the lower end and the upper end of the conductive core; the substrate allowing an upper end of the micro needle to protrude upward therefrom and the lower end of the conductive core to protrude outward therefrom; a conductive member coatedly connected from top of the substrate to the oxide layer; a source electrode disposed at one side of the conductive member; a drain electrode disposed at the other side of the conductive member; an insulation layer coated on top of the conducive member to connect the source electrode and the drain electrode; and a gate electrode disposed at the upper end of the conductive core of the micro needle to allow the source electrode and the drain electrode to be spaced apart from top of the insulation layer, wherein the glucose monitoring module comprises: a voltage applicator connected between the gate electrode of the glucose sensor and the glucose monitoring module; an electric current detector connected to a space between the source electrode and the drain electrode to detect an electric current; a voltage converter for converting the electrical current of the electric current detector into a voltage; a voltage amplifier for amplifying the voltage of the voltage converter; a signal converter for converting an analog signal of the voltage of the voltage amplifier into a data signal; a controller for identifying the data signal of the signal converter; and a radio communication module for transmitting the data signal of the controller outside, and wherein one of the end portions of the conductive core of the micro needle including the upper end of the conductive core which is being protruded upward from the substrate is uncoated with the oxide layer such that electrons move to the conductive members along the micro needle to generate an electric current between the source electrode and the drain electrode when a predetermined voltage is applied to the gate electrode.

\* \* \* \* \*